United States Patent [19]

Light et al.

[11] Patent Number: 6,013,256

[45] Date of Patent: Jan. 11, 2000

[54] METHOD OF PREVENTING ACUTE REJECTION FOLLOWING SOLID ORGAN TRANSPLANTATION

[75] Inventors: Susan Light, MenloPark; Cary Queen, Los Altos, both of Calif.

[73] Assignee: Protein Design Labs, Inc., Fremont, Calif.

[21] Appl. No.: 08/934,841

[22] Filed: Sep. 22, 1997

Related U.S. Application Data

[60] Provisional application No. 60/026,643, Sep. 24, 1996.

[51] Int. Cl.$^7$ .......................... A61K 39/395; A61K 38/13; A01N 45/00; C07J 6/00
[52] U.S. Cl. ..................................... 424/133.1; 424/144.1; 424/154.1; 514/9; 514/26; 530/387.3; 530/388.22; 530/388.75; 530/317; 552/576
[58] Field of Search ........................... 530/387.3, 388.22, 530/388.75, 317; 424/133.1, 144.1, 154.1, 1.45; 514/9, 26; 552/576

[56] References Cited

U.S. PATENT DOCUMENTS

| | | |
|---|---|---|
| 5,011,684 | 4/1991 | Strom . |
| 5,084,391 | 1/1992 | Wijdenes et al. . |
| 5,530,101 | 6/1996 | Queen et al. ......................... 530/387.3 |
| 5,585,089 | 12/1996 | Queen et al. ......................... 424/133.1 |
| 5,693,761 | 12/1997 | Queen et al. ......................... 536/23.53 |
| 5,693,762 | 12/1997 | Queen et al. ......................... 530/387.3 |

FOREIGN PATENT DOCUMENTS

| | | |
|---|---|---|
| WO 89/09622 | 10/1989 | WIPO . |
| WO 93/01289 | 1/1993 | WIPO . |
| WO 93/11238 | 6/1993 | WIPO . |

OTHER PUBLICATIONS

Gaber, AO et al. Am. Surg. 53(7): 407–409, Jul. 1987.

Delmonico, FL et al. Annals of Surgery. 206(5):549–654, Nov. 1987.

Nashan et al., "Reduction of acute cellular rejection by basiliximab (SIMULECT™), in renal allograft recipients," *American Society of Transplant Surgeons*, Presented at 23$^{rd}$ Annual Scientific Meeting (May 14–16, 1997).

Transplantation Proceedings, Second International Congress on Cyclosporine, OLXX, No. 2. Supp, pp. 203–206 (1988).

"Delayed Allograft Rejection In Primates Treated With Anti–il–2 Receptor Monoclonal Antibody Campath–6" Transplantation 45(1):226–228 (1988).

Bone Marrow Transplantation, 21st Annual Meeting of the EBMT and 11th Meeting of the Nurses Group, Abstract Book, DAVOS Switzerland, Mar. 19–23, 1995, vol. 15, Supplement 2 (1995).

Journal of the American Society of Hematology, Thirty–Seventh Annual Meeting, Dec. 1–5, 1995 Seattle, WA, Blood, vol. 86, No. 10 Supplement 1 (1995).

Anasetti et al. "Treatment of Acute Graft–Versus–Host Disease with Humanized Anti–Tac: An Antibody That Binds to the Interleukin–2 Receptor" Blood, 84(4):1320–1327 (1994).

Brown, Jr., P.S. et al., "Anti–Tac–H, a humanized antibody to the interleukin 2 receptor, prolongs the primate cardiac allograft survival" *Proc. Natl. Acad. Sci. USA* 88:2663–2667 (Apr. 1991).

Carpenter, C.B. et al., "Prophylactic use of monoclonal anti–IL–2 receptor antibody in cadaveric renal transplantation" *Am. J. Kidney Diseases* XIV(5), Suppl. 2:54–57 (Nov. 1989).

Hakimi, J. et al., "Humanized Mikβ1, A humanized antibody to the IL–2 Receptor β–chain that acts synergistically with humanized anti–TAC" *J. Immunol.* 151(2):1075–1085 (Jul. 1993).

Herve et al. Treatment of Corticosteriod Resistant Acute Graft–Versus Disease by In Vivo Administration of Anti––Interleukin–2 Receptor Monoclonal Antibody (B–B10), Blood, 75(4):1017–1023 (1990).

Junghans, R.P. et al., "Anti–Tac–H, a humanized antibody to the interleukin 2 receptor with new features for immunotherapy in malignant and immune disorders" *Cancer Res.* 50:1495–1502 (Mar. 1990).

Kirkman, R.L. et al., "Early experience with anti–Tac in clinical renal transplantation" *Transplantation Proc.* 21(1):1766–1768 (Feb. 1989).

Kirkman, R.L. et al., "A randomized prospective trial of anti–Tac monoclonal antibody in human renal transplantation" *Transplantation* 51(1):107–113 (Jan. 1991).

Kupiec–Weglinski, H.J. et al., "Cyclosporine potentiates the immunosuppressive effects of anti–interleukin 2 receptor monoclonal antibody therapy" *Transplantation Proc.* XX, No. 2, Suppl. 2:207–216 (Apr. 1988).

Kupiec–Weglinski et al., "Interleukin 2 Receptor–Targeted Therapy–Rationale and Applications in Organ Transplantation" Transplantation 46(6):785–792 (1988).

Nashan et al., "Immunoprophylaxis with a Monoclonal Anti–IL–2 Receptor Antibody in Liver Transplant Patients" Transplantation 61(4):546–554 (1996).

Queen et al. "A Humanized Antibody That Binds to the Interleukin 2 Receptor" Proc. Natl. Acad. Sci 86:10029–10033 (1989).

Reed, M.H. et al., "Prolongation of primate renal allograft survival by anti–Tac, an anti–human IL–2 receptor monoclonal antibody" *Transplantation* 47(1):55–59 (Jan. 1989).

Rose et al. "A Chimeric Mouse/Human Anti–IL–2 Receptor Antibody With Enhanced Biological Activities" Molecular Immunology 29(1):131–144 (1992).

Rose et al. "Differential Effects of a Murine and Chimeric Mouse/Human Anti–Interleukin–2 Receptor Antibody on Human T–Cell Proliferation" Immunology 76:452–459 (1992).

Soulillou et al. "Prevention of Rejection of Kidney Transplants by Monoclonal Antibody Directed Against Interleukin 2" The LANCET, pp. 1339–1342 (1987).

Soulillou et al. "Randomized Controlled Trail of a Monoclonal Antibody Against The Interleukin–2 Receptor (33B3.1) As Compared with Rabbit Antithymocyte Globulin For Prophylaxis Against Rejection of Renal Allografts" The New England Journal of Medicine 322(17):1175–1182 (1990).

Soulillou et al. "Monoclonal Anti–IL2–Receptor in Organ Transplantation" Transplant Int 2:46–52 (1989).

Strom et al. "Toward More Selective Therapies to Block Undesired Immune Responses" Kidney International, 35:1026–1033 (1989).

Ueda et al., "Differential Effects of Interleukin 2 Receptor-Targeted Therapy on Heart and Kidney Allografts in Rats" Transplantation 49(6):1124–1129 (1990).

Waldmann, T.A., "The IL–2/IL–2 receptor system: A target for rational immune intervention" *Immunol. Today* 14(6):264–270 (1993).

Waldmann et al., "The Multichain Interleukin–2 Receptor: A Target for Immunotherapy of Patients Receiving Allografts" American Journal of Kidney Diseases XIV(5) Suppl 2, 45–53 (1989).

Waldmann et al., "Lymphokine Receptor–Directed Therapy: A Model of Immune Intervention" Journal of Clinical Immunology 10(6): 19S–29S (1990).

Vincenti, et al., Proc. 14th Annual Meeting of the Amer. Soc. of Transplant Physicians, Chicago, IL, May 14–17, 1995, p. 90 (abstract 68).

Bickel et al., "Differential Regulation Of Colony–Stimulating Factors And Interleukin 2 Production By Cyclosporin A", *Proc. Natl. Acad. Sci. USA,* 84(10):3274–3277 (1987).

Clipstone et al., "Identification Of Calcineurin As A Key Signalling Enzyme In T–Lymphocyte Activation", *Nature,* 357(6380):695–697 (1992).

Depper et al., "Blockade Of The Interleukin–2 Receptor By Anti–Tac Antibody: Inhibition Of Human Lymphocyte Activation", *J. Immunol.,* 131(2):690–696 (1983).

Kirkman et al., "Administration Of An Anti–Interleukin 2 Receptor Monoclonal Antibody Prolongs Cardiac Allograft Survival In Mice", *J. Exp. Med.,* 162(1):358–362 (1985).

Kovarik et al., "Disposition Of Basiliximab, An Interleukin–2 Receptor Monoclonal Antibody, In Recipients Of Mismatched Cadaver Renal Allografts", *Transplantation,* 64(12):1701–1705 (1997).

Nashan et al., "Randomised Trial Of Basiliximab Versus Placebo For Control Of Acute Cellular Rejection In Renal Allograft Recipients", *Lancet,* 350(9086):1193–1198 (1997).

Schreiber et al., "The Mechanism Of Action Of Cyclosporin A And FK506", *Immunol. Today,* 13(4):136–142 (1992).

Shapiro et al., "Monoclonal Anti–IL–2 Receptor Antibody In Primate Renal Transplantation", *Transplant. Proc.,* 19(1 Pt. 1):594–598 (1987).

Vincenti et al., "A Phase I Trial Of Humanized Anti–Interleukin 2 Receptor Antibody In Renal Transplantation", *Transplantation,* 63(1):33–38 (1997).

*Physicians' Desk Reference,* 52nd Edition, 1998, pp. 1971–1974.

Zlabinger et al., "Cytokine Release And Dynamics Of Leukocyte Populations After CD3/TCR Monoclonal Antibody Treatment", *J. Clin. Immunol.,* 12(3):170–177 (1992).

*Primary Examiner*—David Saunders
*Assistant Examiner*—F. Pierre VanderVegt
*Attorney, Agent, or Firm*—Townsend & Townsend & Crew LLP

[57] ABSTRACT

The invention provides methods of preventing acute rejection following renal or other solid organ transplantation. The methods entail administering, e.g., intravenously, to a transplant patient a monoclonal antibody which binds to the p55 subunit of the human interleukin-2 (IL-2) receptor of human T lymphocytes. The monoclonal antibody is preferably a chimeric or humanized antibody that blocks binding of IL-2 to the IL-2 receptor. In some methods, a single dose of about 1 mg/kg of antibody is administered about every other week, commencing immediately prior to transplantation and continuing until 8 weeks after transplantation.

23 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 116 amino acids
      (B) TYPE: amino acid
      (C) STRANDEDNESS: single
      (D) TOPOLOGY: unknown (ii) MOLECULE TYPE: protein (iii) HYPOTHETICAL: NO (ix) FEATURE:
      (A) NAME/KEY: Protein
      (B) LOCATION: 1..116
      (D) OTHER INFORMATION: /note= "Variable region of the PDL humanized anti-Tac antibody heavy chain."

(xi) SEQUENCE DESCRIPTION: SEQ ID NO:1:

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Ile
            35                  40                  45

Gly Tyr Ile Asn Pro Ser Thr Gly Tyr Thr Glu Tyr Asn Gln Lys Phe
     50                  55                  60

Lys Asp Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
               100                 105                 110

Thr Val Ser Ser
           115
```

(2) INFORMATION FOR SEQ ID NO:2:

(i) SEQUENCE CHARACTERISTICS:
      (A) LENGTH: 106 amino acids
      (B) TYPE: amino acid

```
        (C) STRANDEDNESS: single
        (D) TOPOLOGY: unknown (ii) MOLECULE TYPE: protein (iii) HYPOTHETICAL: NO (ix) FEATURE:
        (A) NAME/KEY: Protein
        (B) LOCATION: 1..106
        (D) OTHER INFORMATION: /note= "Variable region of the PDL
            humanized anti-Tac antibody light chain."

(xi) SEQUENCE DESCRIPTION: SEQ ID NO:2:

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
            85                  90                  95

Phe Gly Gln Gly Thr Lys Val Glu Val Lys
            100                 105
```

METHOD OF PREVENTING ACUTE REJECTION FOLLOWING SOLID ORGAN TRANSPLANTATION

CROSS-REFERENCE TO RELATED APPLICATION

The present application derives priority from U.S. Ser. No. 60/026,643, filed Sep. 24, 1996, which is incorporated by reference in its entirety for all purposes.

FIELD OF INVENTION

This invention relates generally to the use of a monoclonal antibody which binds to the p55 subunit of the human interleukin-2 ("IL-2") receptor of human T lymphocytes. Specifically, a genetically engineered, chimeric or humanized monoclonal antibody which binds to the p55 subunit of the IL-2 receptor of human T lymphocytes is used to prevent acute rejection following renal or other solid organ transplantation by intravenous administration of the antibody to a transplant patient.

BACKGROUND

Renal transplantation is the definitive therapy for chronic renal failure and has improved the quality of and prolonged the life of thousands since its inception over three decades ago. Despite significant advances in understanding of tissue typing and immunosuppression and the availability of better immunosuppressive agents, acute rejection remains a serious clinical problem. In the absence of successful therapies, rejection will lead to graft failure in some patients, requiring reinstitution of dialysis and the search for another donor kidney. With the use of cyclosporine in conjunction with other immunosuppressive agents, the one-year graft survival rate for cadaver allografts is in the range of 80%, but graft half-life remains less than optimal in the range of 7.2 years. Kirkman et al., *Transplantation*, 1991:51:107–113. Other types of solid organ transplantation, e.g., heart, liver and lung, also save the lives of thousands of patients each year, but here also acute rejection remains a serious clinical problem only partially controlled by current immunosuppressive drugs.

Current immunosuppressive therapy for acute rejection associated with renal or other solid organ transplantation consists of multiple drugs that interfere with the function of the immune system at various levels. In addition to the complications of over-immunosuppression that may result from the use of multiple drugs, each has its own unique toxicity profile, which may limit its usefulness.

T lymphocytes are known to play a key role in allograft rejection. Activated T lymphocytes have been identified as IL-2 receptor bearing cells. Several murine anti-IL-2 receptor antibodies have been administered in clinical trials for the prophylaxis and treatment of allograft rejection. Carpenter, CB et al., *Am J. Kid Dis.* 1989:14:54–57; Kirkman, RL et al., *Transplantation*, 1991:51:107–113 (anti-Tac); Soulillou, PJ et al., *Lancet*, Jun. 13, 1987:1339–1342; Soulillou, JP et al., *N Eng J Med*, 1990:322:1175–1182 (33B3.1); Herve P et al., *Blood*, 1990:75:1017–1023 (B–B10); Nashan et al., Transplantation, 1996:61:546–554.

Murine anti-Tac is a monoclonal antibody that binds to the p55 subunit of the IL-2 receptor of human T and B lymphocytes, blocking the formation of the high-affinity IL-2 receptor and subsequent activation by IL-2. The ability of murine anti-Tac ("MAT") to decrease the number of acute rejection episodes and to delay the first rejection episode following cadaveric renal allograft has been analyzed. Kirkman, RL et al., *Transplantation*, 1991:51:107–113. For 80 patients randomized to receive either standard immunosuppressive therapy (cyclosporine 8 mg/kg/day, prednisone, and azathioprine) or a reduced dose of cyclosporine (4 mg/kg/day), prednisone, azathioprine, and MAT for 10 days post transplantation, the number of patients experiencing an acute rejection episode in the first 10 days post transplant was significantly less in the MAT group as compared with the standard group (5/40 vs. 21/40, p<0.001). In addition, the time to the first rejection episode was greater in the MAT group (12.5 days vs. 7.6 days, p<0.05). However, eventually, the number of rejection episodes between the two groups was not statistically different: 14/40 in the MAT group and 24/40 in the standard group. Further, antibodies to MAT were detected in 7 of 10 patients tested.

Development of an immunogenic response is typical when a mouse antibody is injected into human patients. That is, the injected mouse antibodies are recognized by the immune system as foreign proteins and provoke a human anti-mouse antibody (HAMA) response, which rapidly neutralizes the mouse antibodies and renders them ineffective for further therapy. It has been proposed that the HAMA problem can be reduced or eliminated by use of genetic engineering to transform mouse monoclonal antibodies into more human-like antibodies, utilizing the understanding of antibody structure that scientists have obtained.

Zenapax® (dacliximab) is a humanized anti-Tac ("HAT") antibody, a humanized form of murine anti-Tac described in U.S. Pat. Nos. 5,530,101 and 5,585,089 and Queen et al. 1989:86:1029–10033, all of which are incorporated herein by reference. HAT comprises heavy and light chain variable domains having amino acid sequences designated SEQ. ID. No. 1 and SEQ. ID. No. 2 respectively. Studies of HAT in primate transplant models have reported HAT to be less immunogenic than MAT and to have a longer half-life. Hakimi et al., J. Immun. 1991:147:1352–1359.

The safety and pharmacokinetics of a single IV administration of HAT has been evaluated in a Phase I study. Six patients having Tac-bearing tumors received a single dose of Zenapax® and were followed for 56 days. Four patients received 0.5 mg/kg, and two received 1.0 mg/kg. The only HAT-related adverse events reported were hives, flank pain, and lower extremity pain and edema in one patient who received 0.5 mg/kg of Zenapax®. No tumor responses were observed. One patient who received 0.5 mg/kg of HAT developed an anti-idiotypic antibody to HAT®.

A second phase I study in patients with steroid-resistant acute graft-versus-host disease ("GVHD") was conducted at two centers. Anasetti, C. et al., *Blood*, 1994:84:1320–1327. One center was Fred Hutchinson Cancer Research Center in Seattle, Wash. A second center was Vancouver General Hospital in Vancouver, Canada. In the published study, between the two centers, four patients received a single dose of HAT of 0.5 mg/kg, four patients received a single dose of Zenapax® of 1.0 mg/kg, and twelve patients received a single dose of Zenapax® of 1.5 mg/kg, with a maximum dose of 100 mg. No serious adverse events related to HAT were noted. The only two adverse events felt to be possibly related to HAT were diaphoresis in one patient and chills in another, both at the 0.5 mg/kg level. The protocol allowed for re-treatment at the same dose level, and eight patients received a second dose. No acute adverse events were reported with re-administration of Zenapax®. Patients were evaluated for response on day 29, and 4 had a complete response and 4 had a partial response. Responses were seen at all dose levels, and no dose response relationship was seen. Fluorescent activated cell sorter analysis of peripheral blood lymphocytes showed that HAT was bound to the Tac (p55) portion of the IL-2 receptor for up to 28 days following a single dose of Zenapax®. All but one patient who survived >100 days developed chronic GVHD. None of the patients developed anti-HAT antibodies.

Additional patients with steroid-resistant GVHD were treated with a single dose of Zenapax® in 3 centers in Italy. Pinto R. M., 21st Meeting of the EMBT, Davos, Switzerland, March 1995. Patients were followed for safety, efficacy and pharmacodynamics. No serious adverse events related to HAT were reported, and 3 patients achieved a response.

A phase II/III, blinded, placebo-controlled, multidose trial for the prevention of acute GVHD in bone marrow transplantation was conducted at 12 centers. Anasetti, C., Blood 1995:86, Supplement 1:621a. In addition to a standard immunosuppressive regimen of cyclosporine and methotrexate to prevent GVHD, patients were treated with placebo, Zenapax® 0.3 mg/kg, or Zenapax® 1.2 mg/kg weekly for five doses beginning the day before bone marrow transplantation. However, no significant difference in the incidence of acute GVHD in the placebo and Zenapax-treated groups was observed, that is, Zenapax® was not effective in the prevention of graft-versus-host disease in this study.

A phase I, randomized, open label, multidose study in patients receiving first renal transplants was conducted at two centers. The purpose of the study was to evaluate the safety, pharmacokinetics-dynamics and immunosuppressive effect of HAT. In one center, 12 patients were evaluated. Vincenti, F. et al., *Proceedings of the 14th Annual Meeting of the American Society of Transplant Physicians*, Chicago, Ill., May 14–17, 1995, p. 90 (abstract 68); Vincenti et al., Transplantation 1997:63:33–38. Ten patients received living related transplants (3 HLA identical and 7 one and zero haplotype match) and two patients received cadaveric transplants. Of the 12 patients, 4 received 0.5 mg/kg/week of Zenapax®; 3 received 0.5 mg/kg/every other week of Zenapax®; 2 received 1 mg/kg/week of Zenapax®; and 3 received 1 mg/kg/every other week of Zenapax®. All three patients receiving 1 mg/kg/every other week of Zenapax® received living related transplants. Zenapax® was administered intravenously over 30 minutes to all patients in combination with standard three-drug immunosuppressive therapy (cyclosporine, azathioprine, and prednisone), for a total of five doses. The first dose of Zenapax® was given within 12 hours prior to transplantation and the 4 additional doses were given in the weeks following transplantation. No serious adverse events possibly or probably related to HAT have been reported. One rejection episode was experienced on day 7 by a patient who received a cadaveric transplant and had been randomized to receive Zenapax® at a dose of 0.5 mg/kg/every other week. One patient developed low-titer anti-HAT antibodies. Pharmacokinetics-dynamics results indicated that Zenapax® given at 1 mg/kg/every other week results in good saturation of Tac receptors. Based on this study HAT appears to be safe and well tolerated by patients. However, no conclusions on the efficacy of Zenapax for prevention of kidney transplant rejection could be drawn from this small, phase I study which had no placebo control group.

SUMMARY OF THE INVENTION

The invention provides methods of preventing acute rejection following transplant of a kidney or other solid organ. Some such methods entail administering to a transplant patient a therapeutically effective dosage of a chimeric or humanized monoclonal antibody that binds to the p55 subunit of the human interleukin-2 (IL-2) receptor and inhibits binding of IL-2 to an IL-2 receptor. In some methods, the monoclonal antibody is a humanized antibody. For example, the humanized antibody can be the humanized anti-Tac antibody having a heavy chain variable region designated SEQ. ID. No. 1 and a light chain variable region designated SEQ. ID. No. 2, or other humanized antibody that competes with this anti-Tac antibody for binding to the p55 subunit of the IL-2 receptor. In some methods, the monoclonal antibody is administered in combination with an effective dosage of at least one immunosuppressive agent other than monoclonal antibody. For example, the immunosuppressive agent can be mycophenolate mofetil, cyclosporine, methotrexate, azathioprine, or a corticosteroid. Typically, monoclonal antibodies used in the methods have shown in a clinical trial a statistically significant reduction in rejection episodes for the 6 months following transplantation compared with administering cyclosporine and corticosteroid without the monoclonal antibody. In some methods, the condition of the patient is monitored during and after antibody administration to observe a reduction in rejection episodes attributable to administration of the monoclonal antibody. In some methods, a single dose of about 1 mg/kg of antibody is administered intravenously about every other week, commencing at the time of transplantation and continuing until at least 8 weeks after transplantation.

The invention further provides methods of reducing the incidence of rejection episodes following a renal transplant. The methods entail administering to the patient a therapeutically effective dose of a genetically engineered monoclonal antibody that binds to the p55 unit of the IL-2 receptor with an affinity constant of at least $10^8$ $M^{-1}$. Often genetically engineered antibodies contain CDR regions from a mouse antibody, in which case, such genetically engineered monoclonal antibodies are less immunogenic than the mouse antibody in primates.

The invention further provides methods of preventing acute rejection following transplant of a solid organ. The methods entail administering to a patient in need of such prevention a therapeutically effective dose of a non-immunogenic genetically engineered, chimeric or humanized monoclonal antibody that competitively inhibits binding of the humanized anti-Tac antibody comprising a heavy chain variable region designated SEQ. ID. No. 1 and a light chain variable region designated SEQ. ID. No. 2 to the p55 subunit of the human interleukin-2 (IL-2) receptor.

DETAILED DESCRIPTION

The present invention provides methods of preventing acute rejection following transplantation of the kidney or other solid organ. The methods entail administering a monoclonal antibody which binds to the p55 subunit of the human interleukin-2 (IL-2) receptor on human T lymphocytes to a transplant patient. Monoclonal antibodies used in the methods include humanized and chimeric antibodies and other antibodies produced by genetic engineering.

I. Antibodies (1) Specificity and Affinity

Monoclonal antibodies useful in the claimed methods typically bind to the p55 subunit of the IL-2 receptor with an affinity of at least $10^8$ $M^{-1}$ and preferably $10^9$ $M^{-1}$ or greater. Such monoclonal antibodies are typically humanized or chimeric antibodies, or are otherwise produced by genetic engineering methods. Preferred monoclonal antibodies bind to the same or overlapping epitope as the anti-Tac and humanized anti-Tac antibodies. Two antibodies bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay (see, e.g., Junghans et al., *Cancer Res.* 1990:50:1495–1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Monoclonal antibodies useful in the invention block binding of IL-2 to the IL-2 receptor or its p55 subunit. That is, addition of the antibody at a concentration of 0.1, 0.5, 1, 2, 5, 10 or 20 ug/ml inhibits binding of IL-2 to the p55 subunit or IL-2 receptor on suitable cells (e.g., HuT-102, YT-S2, or PHA blasts) by about at least 50% but preferably 75%, 90% or even 99%, as assayed by methods well known in the art (see Hakimi et al., *J. Immunol.* 1993:151:1075–1085 and Junghans et al., supra, both of which are herein incorporated by reference). Preferred monoclonal antibodies at concentrations of 1, 5, 10 or 20 $\mu$g/ml inhibit or block IL-2-dependent proliferation of appropriate cells by 50%, 75%, 90% or greater, for example of PHA stimulated peripheral blood mononuclear cells (PBMC), i.e., PHA blasts, or PBMC stimulated by tetanus toxoid or other antigen or mixed lymphocyte reaction (MLR), as assayed by art-known techniques (Hakimi et al., Junghans et al., supra).

Examples of antibodies, binding to the p55 subunit of the human interleukin-2 (IL-2) receptor of human T lymphocytes, and useful in the invention include chimeric anti-Tac antibody, described in patent application PCT/US89/01578; RFT5 chimeric antibody, described in EP 449 769 B1; BT563 described in Nasham, et al., *Transplantation*, 1996: 61: 546–554; a chimeric or humanized form of antibody 33B3.1 (Soulillou et al., *New Eng. J. Med.* 1990:322:1175–1182); and most preferably, humanized anti-Tac described in U.S. Pat. No. 5,530,101 or other humanized versions of anti-Tac. Other such antibodies can be produced by standard immunological and genetic engineering techniques.

(2) General Characteristics

Antibodies are very large, complex molecules (molecular weight of 150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions fold up together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-D space to form the actual antibody binding site which locks onto the target antigen. The position and length of the CDRs have been precisely defined. Kabat, E. et al., U.S. Department of Health and Human Services (1983); Chothia et al., *J. Mol. Biol.*, 196:901 (1987) (the definitions of CDRs provided by Kabat and by Chothia are somewhat different). The part of a variable region not contained in the CDRs is called the framework, which forms the environment for the CDRs.

A humanized antibody is a genetically engineered antibody in which the CDRs (hereinafter reference to CDR can include both the Kabat and Chothia CDRs) from a mouse antibody ("donor antibody", which can also be rat, hamster or other similar species) are grafted onto a human antibody ("acceptor antibody"). Thus, a humanized antibody is an antibody having CDRs from a donor antibody and variable region framework and constant regions from a human antibody. In addition, in order to retain high binding affinity, at least one of two additional structural elements can be employed. See, U.S. Pat. Nos. 5,530,101 or 5,585,089, incorporated herein by reference.

In the first structural element, the framework of the heavy chain variable region of the humanized antibody is chosen to have maximal sequence identity (between 65% and 95%) with the framework of the heavy chain variable region of the donor antibody, by suitably selecting the acceptor antibody from among the many known human antibodies. In the second structural element, in constructing the humanized antibody, selected amino acids in the framework of the human acceptor antibody (outside the CDRs) are replaced with corresponding amino acids from the donor antibody, in accordance with specified rules. Specifically, the amino acids to be replaced in the framework are chosen on the basis of proximity to and contact with the CDRs. For example, the replaced amino acids can be adjacent to a CDR in the donor antibody sequence or within 4–6 angstroms of a CDR in the humanized antibody as measured in 3-dimensional space.

A chimeric antibody is a genetically engineered antibody in which the variable region of a mouse (or other rodent) antibody is combined with the constant region of a human antibody. Such antibodies retain the binding specificity of the mouse antibody, while being about two-thirds human. The proportion of nonhuman sequence present in mouse, chimeric and humanized antibodies suggests that the immunogenicity of a chimeric antibodies is intermediate between mouse and humanized antibodies. However, some chimeric antibodies have been reported to cause little or no HAMA response in human patients (e.g., LoBuglio et al., *Proc. Natl. Acad. Sci. USA* 1991:86:4220–4224), such as chRFT5 (Amlot et al., *Transplantation* 1995:60:748–756).

Other types of genetically engineered antibodies that may have reduced immunogenicity relative to mouse antibodies include but are not limited to single-chain antibodies (Huston et al., Proc. Natl. Acad. Sci. USA 1988:85:5879–5883 and Bird et al., *Science* 1988:242:423–426); antibody fragments such as Fab, (Fab')$_2$ and Fv made using recombinant DNA methods; human antibodies made using phage display methods (Dower et al., WO91/17271; McCafferty et al., WO92/001047; and Winter, WO92/20791) or using transgenic animals (Lonberg et al., WO93/12227; Kucherlapati WO91/10741); bifunctional antibodies (e.g., PCT/US92/10140); and antibodies with altered constant regions (e.g., U.S. Pat. No. 5,624,821).

A genetically engineered antibody is said to have reduced immunogenicity relative to a mouse antibody from which it is derived, or to be less immunogenic, if when injected into humans or other primate species, it on average causes a reduced HAMA response. That is, the recipient generates less than 2-fold, 5-fold, preferably 10- or 100-fold less titer of antibodies against the injected genetically engineered antibody than against the mouse antibody when similarly administered, as measured by standard assays (see, e.g., Hakimi et al., *J. Immunol.* 1991: 147: 1352–1359), especially when administered at least 1, 2, 5 or 14 times in a daily, weekly or every other week regimen. The antibody is said to be (essentially) non-immunogenic if when administered at least 1, 2, 5 or 14 times in a daily, weekly or every other week regimen to humans or other primates, few or no (i.e., less than about 10% or 20% but preferably less than 1% or 2%) recipients develop a detectable or significant HAMA response, or a HAMA response that requires cessation of treatment or renders treatment ineffective. For example, humanized anti-Tac has reduced immunogenicity relative to mouse anti-Tac in monkeys (Hakimi et al., supra) and is (essentially) non-immunogenic in human patients, as shown in the clinical trials described below. A chimeric antibody to the p55 subunit of the IL-2 receptor antibody, chRFT5, is also non-immunogenic in human patients (Amlot et al., op. cit.).

II. Pharmaceutical Compositions

For administration to patients, the genetically engineered, chimeric or humanized monoclonal antibody to p55 are typically formulated in a pharmaceutically acceptable carrier. That is, the antibodies can be used in the manufacture of a medicament for treatment of solid organ transplant patients. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make isotonic. The carrier can also contain excipients such as human serum albumin, polysorbate 80, sugars or amino acids to protect the active protein. The concentration of fusion protein in these formulations varies widely from about 0.1 to 100 mg/ml but is often in the range 1 to 10 mg/ml. The formulated monoclonal antibody is particularly suitable for parenteral administration, and can be administered as an intravenous infusion or by subcutaneous, intramuscular or intravenous injection.

III. Therapeutic Methods

The antibodies of the invention are administered to patients before, during and/or after transplant of a solid organ to reduce, prevent or delay acute organ rejection. The solid organ can be cadaveric or non-cadaveric and is preferably cadaveric. If non-cadaveric, the donor can be living-related or living-unrelated. The donor organ may have 0, 1, 2 or more HLA mismatches with the recipient. For example, the methods are useful for treating renal transplant patients. Such patients may require a renal transplant because of end stage renal disease (ESDR) due to any cause such as glomerulonephritis, polycystic kidney disease, diabetes mellitus or hypertension. The methods of the invention are especially useful when the recipient is at high risk of rejecting the transplant, e.g., for second transplants, poorly HLA matched organs, multiple-organ transplants, and black recipients.

Antibody is administered in a therapeutically effective dosage regime to reduce, prevent or delay the incidence of acute graft rejection following the transplant. In some methods, a single dose of about 1 mg/kg of antibody is administered about every other week, commencing immediately prior to transplantation and continuing until 8 weeks after transplantation, and the maximum amount of antibody administered in a single dose can be about 100 mg. In other methods, the dose is 0.25–0.5 mg/kg, 1.5 mg/kg or a fixed unit dose of, e.g., 5 mg, 10 mg or 20 mg.

Usually between 2 and 5 doses, (e.g., 2, 3, 4 or 5) are administered over a period of about 2 weeks to 2 months in order to prevent (i.e., reduce the incidence of) acute rejection episodes for a period of at least 2 or 3 but preferably 6 or 12 months after transplantation. Alternatively, the monoclonal antibody can be administered daily, biweekly, weekly, every other week, monthly or at some other interval for 1 week, 2 weeks, 4 weeks, 8 weeks, 3–6 months or longer.

Antibody to the p55 subunit of the IL-2 receptor can be administered with a therapeutically effective dosage of one or more additional immunosuppressive agents, such as mycophenolate mofetil (Cellcept®), cyclosporine (in its Sandimmune®, Neoral® or generic forms), methotrexate, azathioprine, prednisone or methylprednisone or other suitable corticosteroid, or tacrolimus, OKT3, anti-lymphocyte globulin (e.g., thymoglobulin) or rapamycin. Preferably, the antibody is administered with a standard immunosuppressive regimen consisting of cyclosporine and prednisone or methylprednisone; or of cyclosporine, azathioprine, and prednisone or methylprednisolone; or with mycophenolate mofetil and corticosteroid with or without cyclosporin. Corticosteriods such as prednisone, methylprednisone, prednisolone and methylprednisolone have similar effects in human patients and can be administered interchangeably by a physician when using the methods of the invention. The data presented in the examples show that administration of monoclonal antibody in combination with a standard immunosuppressive regime can result in a statistically significant reduction in the incidence of (e.g., biopsy-proven) acute rejection episodes in the six-month period following the transplant, compared to the standard immunosuppression alone. Such administration also reduces the mean number of rejection episodes per patient and increases the mean time to first rejection. This treatment regime can also increase graft and/or patient survival when measured after 6 and/or 12 months. These benefits can be achieved without a significant increase in serious adverse events, e.g., infection or lymphoproliferative disorder.

EXAMPLE 1 a. EXPERIMENTAL DESIGN AND CONTROL METHODS

HAT (Zenapax; humanized anti-Tac) was evaluated in a multicenter, randomized, double-blind, placebo controlled trial in patients receiving their first renal allograft from a cadaveric donor. Standard immunosuppressive therapy included cyclosporine A and prednisone or methylprednisone. Patients randomized to the control arm received placebo and those in the active treatment arm received HAT. The incidence of acute rejection episodes in the first 6 months post transplant in both groups was compared and the data evaluated for trends. A total of 275 patients were enrolled in the study, 134 in the placebo arm and 141 in the Zenapax arm.

Patients were randomized to receive in a blinded manner 5 doses of either placebo or 1.0 mg/kg of HAT as a 15 minute intravenous infusion every other week beginning immediately prior to transplant. The maximum dose of study drug was 20 mL which, in the case of those patients receiving HAT, was equivalent to 100 mg of antibody. After the initial pre-transplant dose, subsequent doses of study drug were given within ±2 days from day 14, day 28, day 42 and day 56 of the day of transplant.

b. PATIENT SELECTION CRITERIA

Eligible patients for the protocol were 18 years and older and receiving their first renal allograft from a cadaveric donor. If of child bearing age, patients consented to ensure effective contraceptive for 4 months post transplant and the potential benefits of the transplant outweighed the potential risks.

Patients excluded were:

(a) patient who have received a previous renal allograft;
(b) patients who have received previous treatment with an IL-2 directed monoclonal antibody or other investigational agent that would interfere with the ability to evaluate the safety, efficacy, or pharmacokinetics of HAT;
(c) patients with significant active infection;
(d) patients with a positive T-cell lymphocytotoxic crossmatch using donor lymphocytes and recipient serum;
(e) patients receiving any multiple-organ transplant;
(f) patients whose life expectancy is severely limited by diseases other than renal disease;
(g) patients with a history of cancer (other than non-melanoma skin cancer) within the past 5 years;
(h) patients with a known contraindication to systemic steroids or cyclosporine; and
(i) pregnant or lactating females.

All patients were treated with cyclosporine and prednisone or methylprednisone for the prevention of rejection.

An initial dose of 5 mg/kg bid of cyclosporine or a comparable dose of Neoral was administered orally with adjustment to maintain blood levels in each center's established therapeutic range. The first dose was given perioperatively, from 12 hours pre-transplant to 24 hours post transplant. At the discretion of the investigator during this time period, and whenever the patient was unable to take oral medications, cyclosporine was administered at a dose of 3 mg/kg/d by continuous intravenous infusion. The dose was adjusted to maintain blood levels within the center's established therapeutic range. Patients who experienced delayed function in the immediate post transplant period were withdrawn from the study if other antibody therapy was administered or if cyclosporine was discontinued. Prednisone or methylprednisone was given per center protocol.

The first-line treatment for clinically documented rejection episodes was methylprednisolone, per center protocol. Histologic confirmation of the first episode was obtained within 24 hours of initiating treatment with corticosteroids, and the study drug and other immunosuppressive therapy remained unchanged during this initial rejection therapy. At the discretion of the investigator, azathioprine was given. Biopsy of steroid-resistant rejection and of any subsequent episodes was at the discretion of the investigator. Upon completion of the 3 days of methylprednisolone pulse therapy, the steroid dose was returned to the pre-rejection dose level within 14 days.

OKT3 or other anti-lymphocyte therapy was the second line therapy for rejection and was used as first-line treatment if the investigator felt that the episode was severe enough to require it. The dose of anti-lymphocyte therapy and the duration of therapy was determined by the standard of care at each center. Whenever anti-lymphocyte therapy was administered, cyclosporine, steroids, and the study drugs were continued. The cyclosporine dose was halved until anti-lymphocyte therapy was complete, at which time full-dose cyclosporine was resumed.

d. STUDY PARAMETERS

The primary efficacy parameter was the number of patients who, according to assessments performed at their respective centers, developed histologically documented acute rejection episodes in the first 6 months post transplant. A presumptive diagnosis of an acute episode of rejection was based on one or more of the following clinical findings: Temperature >100° F. orally, graft swelling, graft tenderness, >0.3 mg/dL rise in serum creatinine, rising blood pressure, oliguria, reduced flow of perfusion, extraction or excretion profile on renal scan, or ultrasound findings consistent with rejection Histological confirmation of rejection was required, and the biopsy specimen assessed according to the following Banff schema:

| Biopsy finding | Banff Classification |
| --- | --- |
| Normal, minor changes, or infiltrates without tubular invasion | Normal or other (non-specific changes) |
| Very mild lymphocytic invasion of tubules (tubulitis) | Boderline changes |
| Widespread interstitial infiltrate with moderate invasion of tubules | Mild acute rejection (Grade I) |
| (A) Widespread interstitial infiltrate with severe invasion of tubules and/or | Moderate acute rejection (Grade II) |
| (B) Mild or moderate intimal arteries | |
| Severe intimal arteritis, and/or "transmural" arteritis, fibrinoid change, and medial smooth muscle cell necrosis often with patchy infarction and interstitial hemorrhage. | Severe acute rejection (Grade III) |
| Hyaline arteriolar thickening (new onset, not present in implantation biopsy) and/or extensive isometric vacuolization of tubules, smooth muscle degeneration, thrombotic microangiopathy. | Other, cyclosporine toxicity |
| Tubular cell loss and necrosis, regenerative changes. | "Other, " acute tubular necrosis |
| Interstitial fibrosis, tubular atrophy (new onset aterial fibrous intimal thickening suggests chronic rejection) | Chronic transplant nephropathy ("chronic rejection") (Absent = Grade 0, Mild = Grade 1, Moderate = Grade 2, Severe = Grade 3) |

In the event a core biopsy specimen could not be obtained, diagnosis of rejection was established by analysis of renal allograft aspirate, and assessed as evidence of acute rejection according to the total blast count >0 and a score of >3.0 in a representative aspirate (as judged by the presence of more than 5 tubular cells per field).

Secondary efficacy parameters were:

1. Number of acute rejection episodes per patient in the first 6 months post transplant;
2. Time to first acute rejection episode;
3. Incidence of delayed function;
4. Graft function post transplant;
5. Number of patients with >1 rejection episode in the first 6 months post transplant;
6. Graft failure post transplant;
7. Documented infections in the first 6 months post transplant;
8. Patient survival post transplant;
9. Cumulative dose of prednisone in the first 6 months post transplant;
10. Cumulative dose of OKT3 or other anti-lymphocyte therapy in the first 6 months post transplant; and
11. Post transplant incidence of lymphoproliferative disorders; and 12. Post transplant incidence of malignancies.

The initial acute rejection was defined as a histologically confirmed event that was characterized by one of the above clinical findings for an acute episode of rejection and that resulted in therapy with corticosteroids or anti-lymphocyte therapy. Each subsequent rejection episode was defined as an event that was characterized by one of the above clinical findings for an acute episode of rejection and that resulted in a course of treatment either with higher doses of methylprednisolone or with at least 5 days of anti-lymphocyte therapy.

e. TRIAL MEDICATION

The study was double-blinded.

The formulation contained 5 mg/mL HAT and 0.2 mg/mL Polysorbate-80 in 67 mM phosphate buffer, pH adjusted to 6.9. The appropriate quantity of antibody solution at 5 mg/mL or placebo (maximum 20 mL) was diluted with 50 mL of normal saline in a mini-bag.

The route of administration was intravenous infusion over a period of 15 minutes.

The concentration of antibody was 5 mg protein per milliliter.

Patients received either placebo or HAT beginning immediately prior to transplant and followed by four additional doses, one dose every other week.

f. STATISTICAL CONSIDERATION

Time to first acute rejection episode was analyzed using survival analysis techniques including Kaplan-Meier plots, and log rank test stratified by center. All variables were analyzed using the stratified Mantel-Haenszel test (stratified by center).

The number of acute rejection episodes per patient was analyzed based on normal regression model as well as a Poison regression model.

g. RESULTS

The incidence of biopsy proven rejection in the first six months posttransplant was 47% in the placebo group and 28% in the Zenapax group. This 40% reduction in rejection was significant at a p value of 0.001. In addition, the time to first rejection episode was significantly longer in those patients who received Zenapax (p=0.0001) and the number of rejection episodes per patient (0.51 per patient vs. 0.83 per patient) was significantly less in the Zenapax group (p=0.004). Significantly fewer patients in the Zenapax arm received additional antilymphocytic therapy (11 vs 22 patients, p=0.02). The cumulative dose of corticosteroids showed a significant reduction in the Zenapax arm relative to the placebo arm (p=0.01).

Patient survival at six months after transplantation was improved from 96% for the placebo arm to 100% for the Zenapax arm, while graft survival was improved from 86% to 91%. Patient survival at twelve months after transplantation was improved from 94% for the placebo arm to 99% for the Zenapax arm (p=0.01), while graft survival was improved from 83% to 88%. No specific and particular acute side effects or any allergic reactions in the Zenapax group were noted, and the total number of adverse events in the placebo and Zenapax groups were essentially the same.

EXAMPLE 2 a. EXPERIMENTAL DESIGN AND CONTROL METHODS

HAT was evaluated in a multi center, randomized, double-blind, placebo controlled trial in patients receiving their first renal allograft from a cadaveric donor. Standard immunosuppressive therapy included cyclosporine A, azathioprine, and methylprednisolone. Patients randomized to the control arm received placebo and those in the active treatment arm received HAT. The incidence of acute rejection episodes in the first 6 months post transplant in both groups was compared and the data evaluated for trends. A total of 260 patients were enrolled in the study, 134 in the placebo arm and 126 in the Zenapax arm.

Patients were randomized to receive in a blinded manner 5 doses of either placebo or 1.0 mg/kg of HAT as a 15 minute intravenous infusion every other week beginning immediately prior to transplant. The maximum dose of study drug was 20 mL which, in the case of those patients receiving HAT, was equivalent to 100 mg of antibody. After the initial pre-transplant dose, subsequent doses of study drug were given within ±2 days from day 14, day 28, day 42 and day 56 of the day of transplant.

b. PATIENT SELECTION CRITERIA

Eligible patients for the protocol were 18 years and older and receiving their first renal allograft from a cadaveric donor. If of child bearing age, patients consented to ensure effective contraceptive for 4 months post transplant and the potential benefits of the transplant outweighed the potential risks.

Patients excluded were:

(a) patient who have received a previous renal allograft;

(b) patients who have received previous treatment with an IL-2 directed monoclonal antibody or other investigational agent that would interfere with the ability to evaluate the safety, efficacy, or pharmacokinetics of HAT;

(c) patients with significant active infection;

(d) patients with a positive T-cell lymphocytotoxic crossmatch using donor lymphocytes and recipient serum;

(e) patients receiving any multiple-organ transplant;

(f) patients whose life expectancy is severely limited by diseases other than renal disease;

(g) patients with a history of cancer (other than non-melanoma skin cancer) within the past 5 years; and (h) patients with a known contraindication to systemic steroids, azathioprine, or cyclosporine.

All patients were treated with cyclosporine, azathioprine, and methylprednisolone for the prevention of rejection.

An initial dose of 5 mg/kg bid of cyclosporine (or a comparable dose of Neoral) was administered orally with adjustment to maintain blood levels in each center's established therapeutic range. The first dose was given perioperatively, from 12 hours pre-transplant to 24 hours post transplant. At the discretion of the investigator during this time period, and whenever the patient was unable to take oral medications, cyclosporine was administered at a dose of 3 mg/kg/d by continuous intravenous infusion. The dose was adjusted to maintain blood levels within the center's established therapeutic range. Patients who experienced delayed function in the immediate post transplant period were withdrawn from the study if other antibody therapy was administered or if cyclosporine was discontinued.

Azathioprine was administered at a dose of 4 mg/kg IV in the operating room, then 1.5–2.0 mg/kg/day IV or PO. The daily oral dose was decreased for a white blood of less than 5,000 cells/mm$^3$, but was not increased.

Methylprednisolone was administered as follows: 7 mg/kg IV in the operating room; 3 mg/kg on day 1, 2 mg/kg IV on day 2, tapered to 20–30 mg/day PO by day 30; tapered to 10–20 mg/day by day 90; and tapered to 5–10 mg/day by day 180.

The first-line treatment for clinically documented rejection episodes was methylprednisolone, 7 mg/kg IV daily. Histologic confirmation of the first episode was obtained within 24 hours of initiating treatment with high dose corticosteroids, and the study drug and other immunosuppressive therapy remained unchanged during this initial rejection therapy. Biopsy of steroid-resistant rejection and of any subsequent episodes was at the discretion of the investigator. Upon completion of the 3 days of methylprednisolone pulse therapy, the steroid dose was returned to the pre-rejection dose level within 14 days.

OKT3 or other anti-lymphocyte therapy was the second line therapy for rejection and was used as first-line treatment if the investigator felt that the episode was severe enough to require it. The dose of anti-lymphocyte therapy and the duration of therapy was determined by the standard of care at each center. Whenever anti-lymphocyte therapy was administered, cyclosporine, steroids, and the study drug were continued. At the discretion of the investigator, azathioprine was discontinued and/or the cyclosporine dose was halved until anti-lymphocyte therapy was complete, at which time azathioprine and full-dose cyclosporine was resumed. In addition, methylprednisone was administered at a dose of 8 mg/kg intravenously 1 to 4 hours prior to the first dose of anti-lymphocyte therapy, followed by a taper of steroids over a maximum period of 30 days to the pre-rejection dose level.

d. STUDY PARAMETERS

The primary efficacy parameter was the number of patients who, according to assessments performed at their respective centers, developed historically documented acute rejection episodes in the first 6 months post transplant. A presumptive diagnosis of an acute episode of rejection was based on one or more of the following clinical findings: Temperature >100° F. orally, graft swelling, graft tenderness, >0.3 mg/dL rise in serum creatinine, rising blood pressure, oliguria, reduced flow of perfusion, extraction or excretion profile on renal scan, or ultrasound findings consistent with rejection.

Histological confirmation of rejection was required, and the biopsy specimen assessed according to the following Banff schema:

| Biopsy finding | Banff Classification |
|---|---|
| Normal, minor changes, or infiltrates without tubular invasion | Normal or other (non-specific changes) |
| Very mild lymphocytic invasion of tubules (tubulitis) | Boderline changes |
| Widespread interstitial infiltrate with moderate invasion of tubules | Mild acute rejection (Grade I) |
| (A) Widespread interstitial infiltrate with severe invasion of tubules and/or (B) Mild or moderate intimal arteries | Moderate acute rejection (Grade II) |
| Severe intimal arteritis, and/or "transmural" arteritis, fibrinoid change, and medial smooth muscle cell necrosis often with patchy infarction and interstitial hemorrhage | Severe acute rejection (Grade III) |
| Hyaline arteriolar thickening (new onset, not present in implantation biopsy) and/or extensive isometric vacuolization of tubules, smooth muscle degeneration, thrombotic microangiopathy. | Other, cyclosporine toxicity |
| Tubular cell loss and necrosis, regenerative changes. | "Other," acute tubular necrosis |
| Interstitial fibrosis, tubular atrophy (new onset aterial fibrous intimal thickening suggests chronic rejection) | Chronic transplant nephropathy ("chronic rejection") (Absent = Grade 0, Mild = Grade 1, Moderate = Grade 2, Severe = Grade 3) |

In the event a core biopsy specimen could not be obtained, diagnosis of rejection was established by analysis of renal allograft aspirate, and assessed as evidence of acute rejection according to the total blast count >0 and a score of >3.0 in a representative aspirate (as judged by the presence of more than 5 tubular cells per field).

Secondary efficacy parameters were:
1. Number of acute rejection episodes per patient in the first 6 months post transplant;
2. Time to first acute rejection episode;
3. Incidence of delayed function;
4. Graft function post transplant;
5. Number of patients with >1 rejection episode in the first 6 months post transplant;
6. Graft failure post transplant;
7. Documented infections in the first 6 months post transplant;
8. Patient survival post transplant;
9. Cumulative dose of prednisone in the first 6 months post transplant;
10. Cumulative dose of OKT3 or other anti-lymphocyte therapy in the first 6 months post transplant;
11. Post transplant incidence of lymphoproliferative disorders; and
12. Post transplant incidence of malignancies.

The initial acute rejection was defined as a histologically confirmed event that was characterized by one of the above clinical findings for an acute episode of rejection and that results in therapy with corticosteroids or anti-lymphocyte therapy. Each subsequent rejection episode was defined as an event that was characterized by one of the above clinical findings for an acute episode of rejection and that resulted in a course of treatment either with methylprednisone 7 mg/kg/day or with at least 3 days of OKT3.

e. TRIAL MEDICATION

The Study was Double-blinded.

The formulation contained 5 mg/mL HAT and 0.2 mg/mL Polysorbate-80 in 67 mM phosphate buffer, pH adjusted to 6.9. The appropriate quantity of antibody solution at 5 mg/mL or placebo (maximum 20 mL) was diluted with 50 mL of normal saline in a mini-bag.

The route of administration was intravenous infusion over a period of 15 minutes.

The concentration of antibody was 5 mg protein per milliliter.

Patients received either placebo or HAT beginning immediately prior to transplant and followed by four additional doses, one dose every other week.

f. STATISTICAL CONSIDERATION

Time to first acute rejection episode was analyzed using survival analysis techniques including Kaplan-Meier plots, and log rank test stratified by center. All categorical variables were analyzed using the stratified Mantel-Haenszel test (stratified by center).

The number of acute rejection episodes per patient in the first 6 months was analyzed based on normal regression models as well as a Poisson regression model.

g. RESULTS

The incidence of biopsy proven rejection in the first six months posttransplant was 35% in the placebo group and 22% in the Zenapax group. This 37% reduction in rejection was significant at a p value of 0.03. In addition, the time to first rejection episode was significantly longer in those patients who received Zenapax (p=0.008) and the number of rejection episodes per patient (0.33 vs 0.57 per patient) was significantly less in the Zenapax group (p=0.01).

Patient survival at six months after transplantion was improved from 97% for the placebo arm to 99% for the Zenapax arm, while graft survival was improved from 91% to 98% (p=0.02). Patient survival at twelve months after transplantation was improved from 96% for the placebo arm to 98% for the Zenapax arm, while graft survival was improved from 90% to 95% (p=0.08). Administration of Zenapax was not associated with any immediate side effects, and there was no significant difference in reported and observed adverse events between the placebo and Zenapax treated patients.

All publications and patent applications cited above are herein incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

---

We claim:

1. A method of reducing the incidence of acute rejection episodes following renal transplantation, comprising administering to human patients undergoing renal transplants a therapeutically effective dosage of a chimeric or humanized monoclonal antibody that binds to the p55 subunit of the human interleukin-2 (IL-2) receptor and inhibits binding of IL-2 to an IL-2 receptor, wherein the incidence of acute rejection episodes is reduced in said patients during six months following renal transplantation.

2. The method of claim 1, wherein said monoclonal antibody is a humanized anti-Tac antibody.

3. A method of reducing the incidence of acute rejection episodes following renal transplantation, comprising administering to human patients undergoing renal transplants a therapeutically effective dosage of a chimeric or humanized monoclonal antibody that binds to the p55 subunit of the human interleukin-2 (IL-2) receptor and inhibits binding of IL-2 to an IL-2 receptor, wherein said therapeutically effective dosage causes a reduction in the incidence of acute rejection episodes during at least 6 months following renal transplantation as compared to the incidence of acute rejection episodes during at least 6 months following renal transplantation in patients that have not received said monoclonal antibody.

4. A method of reducing the incidence of acute rejection episodes following renal transplantation, comprising administering to human patients a therapeutically effective dosage of a chimeric or humanized monoclonal antibody that binds to the p55 subunit of the human interleukin-2 (IL-2) receptor and inhibits binding of IL-2 to an IL-2 receptor; and monitoring the incidence of rejection episodes in the patients over a period of at least six months following the transplantation, wherein the incidence of monitored rejection episodes in the patients over the period is reduced in comparison to the incidence of rejection episodes in a population of renal transplant patients administered an immunosuppressive therapy without the monoclonal antibody, the reduction being statistically significant.

5. The method of any one of claims 1, 3 and 4, wherein said monoclonal antibody is a humanized monoclonal antibody.

6. The method of claim 5, wherein said humanized monoclonal antibody competes with a humanized anti-Tac antibody having a heavy chain variable region with the amino acid sequence of SEQ. ID. No. 1 and a light chain variable region with the amino acid sequence of SEQ. ID. No. 2 for binding to the p55 subunit of the IL-2 receptor.

7. The method of claim 6 wherein the therapeutically effective dosage is a single dose of about 1 mg/kg of antibody administered intravenously about every other week, commencing before transplantation and continuing until at least 8 weeks after transplantation.

8. The method of any one of claims 1, 3 and 4, wherein the monoclonal antibody is administered in combination with an effective dosage of at least one immunosuppressive agent other than monoclonal antibody.

9. The method of claim 8, wherein the at least one immunosuppressive agent is selected from the group consisting of mycophenolate mofetil, cyclosporine, methotrexate, azathioprine, a corticosteroid, tacrolimus and rapamycin.

10. The method of claim 9, wherein the corticosteriod is selected from the group consisting of prednisone, methylprednisone, prednisolone, and methylprednisolone.

11. The method of claim 9 wherein the at least one immunosuppressive agent is cyclosporine and corticosteroid.

12. The method of claim 11, wherein the monoclonal antibody has shown in a clinical trial a statistically significant reduction in rejection episodes for the 6 months following transplantation compared with administering cyclosporine and corticosteroid without the monoclonal antibody.

13. The method of claim 11, further comprising monitoring the condition of the patient for a reduction in rejection episodes attributable to administration of the monoclonal antibody.

14. The method of claim 13 wherein the patients receive renal transplants from cadavers.

15. A method of reducing the incidence of acute rejection episodes following renal transplants in patients comprising administering to the patients a therapeutically effective dosage of a genetically engineered monoclonal antibody that binds to the p55 unit of the IL-2 receptor with an affinity constant of at least $10^8$ $M^{-1}$, wherein the incidence of acute rejection episodes is reduced in said patients during six months following renal transplantation.

16. The method of claim 15 wherein said monoclonal antibody comprises the complementarity determining regions (CDRs) from a mouse antibody.

17. The method of claim 16 wherein said monoclonal antibody is less immunogenic than the mouse antibody in primates.

18. The method of claim 17 wherein said monoclonal antibody is humanized anti-Tac.

19. The method of claim 15, wherein the monoclonal antibody is administered in combination with a standard immunosuppressive therapy comprising cyclosporine and corticosteroid to the patients, whereby the incidence of rejection episodes in the patients is reduced over a period of six months compared with the incidence of rejection episodes in renal transplant patients administered the standard immunosuppressive therapy without the monoclonal antibody.

20. The method of claim 19, wherein the monoclonal antibody is administered for between 2 and 12 weeks.

21. The method of claim 15, wherein said affinity constant is at least $10^9$ $M^{-1}$.

22. A method of reducing the incidence of acute rejection episodes during at least three months following transplant of a solid organ, comprising administering to human patients receiving transplants of that organ a therapeutically effective dose of a non-immunogenic genetically engineered, chimeric or humanized monoclonal antibody that competitively inhibits binding of the humanized anti-Tac antibody comprising a heavy chain variable region having the amino acid sequence of SEQ. ID. No. 1 and a light chain variable region having the amino acid sequence of SEQ. ID. No. 2 to the p55 subunit of the human interleukin-2 (IL-2) receptor in combination with an immunosuppressive therapy comprising cyclosporine and corticosteroid to the patient.

23. The method of claim 22, wherein the solid organ is a kidney or liver.

* * * * *

UNITED STATES PATENT AND TRADEMARK OFFICE
CERTIFICATE OF CORRECTION

PATENT NO. : 6,013,256  Page 1 of 2
DATED : January 11, 2000
INVENTOR(S) : Susan Light and Cary Queen It is certified that error appears in the above-indentified patent and that said Letters Patent is hereby corrected as shown below:

Column 2, line 32, insert "*Proc. Natl. Acad. Sci.*', delete "1029" and insert therefor --10029--.

Column 2, line 48, after "HAT", delete "®".

Column 5, line 20, delete "ug/ml", and insert therefor -- $\mu$g/ml --.

Column 7, line 50, delete "[ESDR]", and insert therefor -- [ESRD] --.

Column 8, line 19, delete "cyclosporin", and insert therefor --cyclosporine--.

Column 8, line 20, delete "Corticosterioids", and insert therefor --Corticosteroids--.

Column 10, line 11, delete "Boderline", and insert therefor -Borderline--.

Column 10, line 41, delete "aterial", and insert therefor -arterial--.

Column 13, line 44, delete "Boderline", and insert therefor -Borderline--.

Column 14, line 7, delete "aterial", and insert therefor -arterial--.

Column 15, line 13, delete "transplantion", and insert therefor --transplantation--.

UNITED STATES PATENT AND TRADEMARK OFFICE
CERTIFICATE OF CORRECTION

PATENT NO. : 6,013,256
DATED : January 11, 2000
INVENTOR(S) : Susan Light and Cary Queen It is certified that error appears in the above-indentified patent and that said Letters Patent is hereby corrected as shown below:

In the Claims:

Claim 10, column 18, line 62, delete "corticosteriod", and insert therefor --corticosteroid--.

Claim 13, column 19, line 8, delete "patient", and insert therefor --patients--.

Signed and Sealed this

Thirteenth Day of March, 2001

Attest:

NICHOLAS P. GODICI

Attesting Officer

Acting Director of the United States Patent and Trademark Office